(12) United States Patent
Atiya et al.

(10) Patent No.: US 11,202,574 B2
(45) Date of Patent: *Dec. 21, 2021

(54) APPARATUS FOR DENTAL IMAGING

(71) Applicant: Align Technology, Inc., San Jose, CA (US)

(72) Inventors: Yossef Atiya, Maccabim (IL); Tal Verker, Ofra (IL); Nir Makmel, Tel Aviv (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/191,579

(22) Filed: Mar. 3, 2021

(65) Prior Publication Data
US 2021/0186335 A1   Jun. 24, 2021

Related U.S. Application Data

(63) Continuation of application No. 17/037,398, filed on Sep. 29, 2020, which is a continuation of application
(Continued)

(51) Int. Cl.
| | |
|---|---|
| *A61B 5/00* | (2006.01) |
| *G02B 13/16* | (2006.01) |
| *G02B 6/26* | (2006.01) |
| *G01B 11/24* | (2006.01) |
| *G01B 11/245* | (2006.01) |
| *A61C 9/00* | (2006.01) |
| *G02B 6/00* | (2006.01) |
| *F21V 8/00* | (2006.01) |

(Continued)

(52) U.S. Cl.
CPC .......... *A61B 5/0088* (2013.01); *A61C 9/0066* (2013.01); *G01B 11/24* (2013.01); *G01B 11/245* (2013.01); *G02B 5/04* (2013.01); *G02B 6/0006* (2013.01); *G02B 6/0046* (2013.01); *G02B 6/262* (2013.01); *G02B 13/16* (2013.01); *G02B 23/2461* (2013.01); *G01B 2210/50* (2013.01); *G02B 2006/0098* (2013.01)

(58) Field of Classification Search
None
See application file for complete search history.

(56) References Cited

U.S. PATENT DOCUMENTS 4,575,805 A * 3/1986 Moermann ........ A61C 13/0004
700/163
5,372,502 A * 12/1994 Massen .................. G01B 11/24
433/215

(Continued)

*Primary Examiner* — Michelle M Iacoletti
*Assistant Examiner* — Jarreas C Underwood
(74) *Attorney, Agent, or Firm* — Lowenstein Sandler LLP

(57) ABSTRACT

An apparatus for dental imaging comprises a light source for generating light, an optics system for focusing the light, and a probe head. The light source, the optics system and the probe head are arranged such that the light passes through the optics system, passes through the probe head, and exits the probe head. The optics system is configured such that, upon entering the probe head, an outermost chief ray of the light with respect to an optical axis of the optics system is divergent to the optical axis and an outermost marginal ray of the light with respect to the optical axis is parallel or divergent to the optical axis.

27 Claims, 3 Drawing Sheets

Related U.S. Application Data

No. 16/820,505, filed on Mar. 16, 2020, now Pat. No. 10,835,128, which is a continuation of application No. 14/741,172, filed on Jun. 16, 2015, now Pat. No. 10,772,506.

(60) Provisional application No. 62/021,608, filed on Jul. 7, 2014.

(51) Int. Cl.
*G02B 5/04* (2006.01)
*G02B 23/24* (2006.01)

(56) References Cited

U.S. PATENT DOCUMENTS

| | | | |
|---|---|---|---|
| 6,099,314 A | 8/2000 | Kopelman et al. | |
| 6,263,234 B1 * | 7/2001 | Engelhardt | A61B 5/0088 |
| | | | 600/476 |
| 6,334,772 B1 | 1/2002 | Taub et al. | |
| 6,334,853 B1 | 1/2002 | Kopelman et al. | |
| 6,463,344 B1 | 10/2002 | Pavlovskaia et al. | |
| 6,542,249 B1 | 4/2003 | Kofman et al. | |
| 6,594,539 B1 * | 7/2003 | Geng | A61B 1/247 |
| | | | 264/16 |
| 6,633,789 B1 | 10/2003 | Nikolskiy et al. | |
| 6,664,986 B1 | 12/2003 | Kopelman et al. | |
| 6,697,164 B1 * | 2/2004 | Babayoff | A61B 1/00096 |
| | | | 356/609 |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,138,640 B1 * | 11/2006 | Delgado | G01N 21/15 |
| | | | 250/372 |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,872,760 B2 * | 1/2011 | Ertl | G01B 11/24 |
| | | | 356/479 |
| 7,916,911 B2 | 3/2011 | Kaza et al. | |
| 8,054,556 B2 * | 11/2011 | Chen | G02B 17/08 |
| | | | 359/649 |
| 8,108,189 B2 | 1/2012 | Chelnokov et al. | |
| 8,244,028 B2 | 8/2012 | Kuo et al. | |
| 8,279,450 B2 * | 10/2012 | Oota | A61B 1/0019 |
| | | | 356/601 |
| 8,488,113 B2 * | 7/2013 | Thiel | G01J 3/02 |
| | | | 356/73 |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 * | 2/2016 | Atiya | G01B 11/25 |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,444,981 B2 * | 9/2016 | Bellis | H04N 5/2252 |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,513,470 B1 * | 12/2016 | Weaver | G02B 21/367 |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 * | 9/2020 | Atiya | G02B 13/16 |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 2003/0048540 A1 * | 3/2003 | Xie | A61B 3/102 |
| | | | 359/637 |
| 2005/0100333 A1 * | 5/2005 | Kerschbaumer | A61B 1/0676 |
| | | | 396/16 |
| 2010/0157019 A1 | 6/2010 | Schwotzer et al. | |
| 2016/0000332 A1 * | 1/2016 | Atiya | G01B 11/24 |
| | | | 433/29 |
| 2019/0029784 A1 | 1/2019 | Moalem et al. | |
| 2019/0231492 A1 | 8/2019 | Sabina et al. | |
| 2019/0388193 A1 | 12/2019 | Ofer et al. | |
| 2019/0388194 A1 | 12/2019 | Yossef et al. | |
| 2020/0281700 A1 | 9/2020 | Kopelman et al. | |
| 2020/0281702 A1 | 9/2020 | Kopelman et al. | |
| 2020/0315434 A1 | 10/2020 | Kopelman et al. | |
| 2020/0349698 A1 | 11/2020 | Mikhail et al. | |
| 2020/0349705 A1 | 11/2020 | Mikhail et al. | |
| 2020/0404243 A1 | 12/2020 | Saphier et al. | |
| 2021/0030503 A1 | 2/2021 | Shalev et al. | |
| 2021/0059796 A1 | 3/2021 | Weiss et al. | |
| 2021/0068773 A1 | 3/2021 | Moshe et al. | |

* cited by examiner

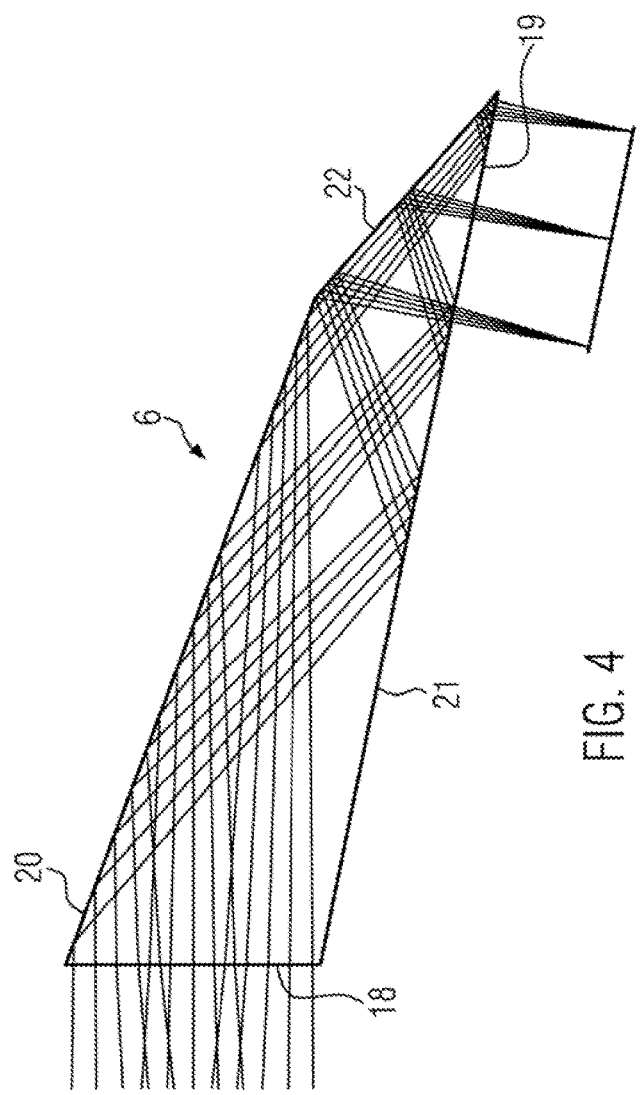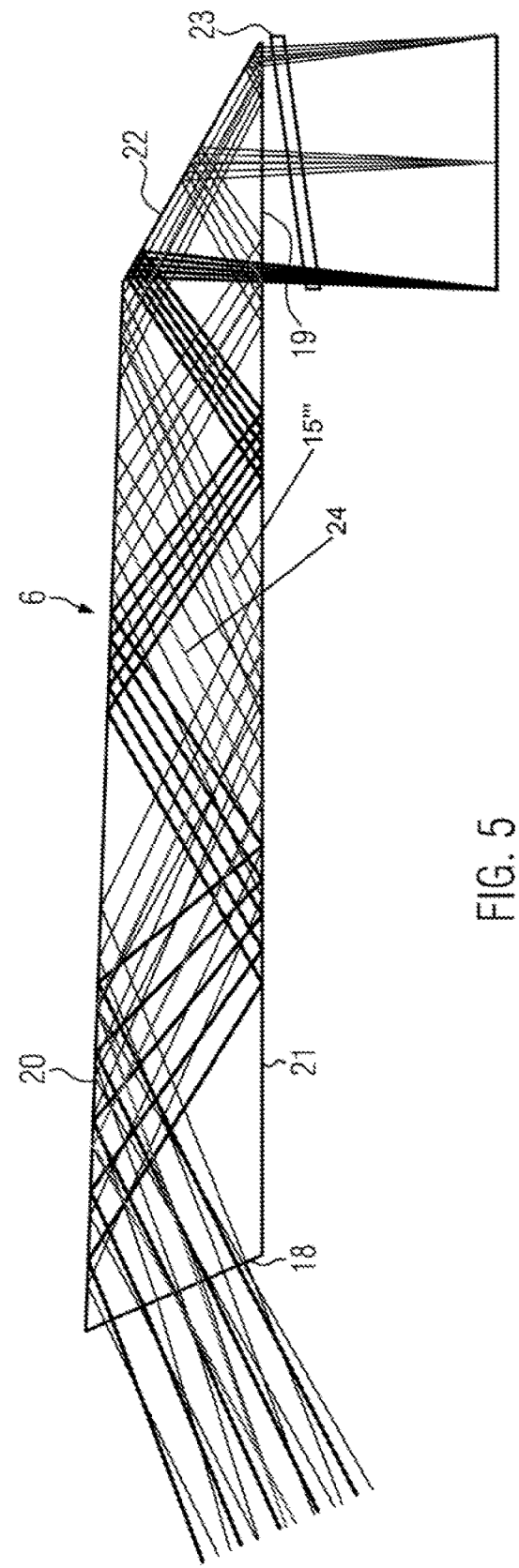

APPARATUS FOR DENTAL IMAGING

CROSS REFERENCE

This application is a continuation of U.S. patent application Ser. No. 17/037,398 filed Sep. 29, 2020, which is a continuation of U.S. patent application Ser. No. 16/820,505 filed Mar. 16, 2020, which is a continuation of U.S. patent application Ser. No. 14/741,172, filed Jun. 16, 2015, which claims the benefit of U.S. Provisional Application No. 62/021,608, filed Jul. 7, 2014, the contents of each of which are hereby incorporated by reference in their entirety.

FIELD OF THE INVENTION

Embodiments of the present invention are directed to methods and apparatus for dental imaging, such as for measuring surface topology of teeth.

BACKGROUND

In the fields of orthodontics and prosthodontics, different methods are known to determine a current teeth topology in a patient's mouth. One of the methods involves taking an impression of a patient's dentition. Using this impression, a plaster cast is made, representing a (positive) physical teeth model. This physical teeth model may then be used for a subsequent treatment plan.

If CAD (computer-aided design) and/or CAM (computer-aided manufacturing) techniques are to be employed, a digital dataset corresponding to the teeth may be obtained by scanning. For example, the (positive) physical teeth model in form of the plaster cast or a (negative) physical teeth model in form of the impression may be scanned or imaged using x-rays, computed tomography, magnetic resonance imaging, or laser scanning apparatuses. With the thus obtained image data, a computer model of the teeth or a part thereof may be established. However, such methods and apparatus can be somewhat time consuming and more expensive than would be ideal.

As an alternative, teeth in a patient's mouth may be imaged directly. For this purpose, different imaging apparatuses are known.

The prior apparatus for non-contact imaging with a probe having a sensing face have been less than ideal in at least some respects. The prior probe devices can be somewhat larger than would be ideal, and may have a large intraoral front tip which can make the prior devices somewhat cumbersome to use in at least some instances. Although an array of incident light beams passing through focusing optics can be used, the larger than ideal probe heads of such devices can provide less than ideal measurements of the oral cavity of a patient. Also, the prior devices that rely on beams to generate illuminated spots on the structure and the intensity of returning light rays propagating along an optical path can be somewhat cumbersome to use and maintain and can be somewhat more costly to manufacture than would be ideal.

Although three-dimensional (3D) data acquisition using triangulation has been proposed, such devices can be less compact than would be ideal and can be somewhat difficult to place in the mouth of the patient. Also, such devices can require alignment and can be less accurate and reliable than would be ideal in at least some instances.

In light of the above, improved methods and apparatus for measuring surfaces such as the intraoral cavity are needed. Ideally such methods and apparatus will overcome at least some of the deficiencies of the prior methods and apparatus and be more accurate, reliable, compact, easier to use with the patient's mouth and less costly than the prior devices.

SUMMARY

In accordance with embodiments, an apparatus for confocal imaging is provided, which may comprise an illumination module for generating an array of light beams, an optics system for confocal focusing of the array of light beams, and a probe head with a light-guiding part having an entrance face and an exit face. The illumination module, the optics system, and the probe head can be arranged such that the array of light beams from the illumination module passes through the optics system, enters the light-guiding part via the entrance face, and exits the light-guiding part via the exit face. Embodiments disclosed herein provide probes having decreased size which can facilitate measurement of surfaces which can be difficult to reach with prior devices such as an oral cavity of a patient. The embodiments disclosed herein also have the advantage of providing improved accuracy and reliability with decreased manufacturing costs. In many embodiments, a plurality of beams is directed toward a measurement surface in which each of the plurality of beams extends to a focal point and comprises a chief ray. The chief rays of the plurality of beams can diverge from each other between the probe and the focal points in order to decrease the size of the probe and inhibit spread of the outermost marginal rays. In many embodiments, the confocal imaging system comprises a non-telecentric configuration such that the off-axis chief ray angles of the light beams exiting the probe have an opposite orientation with respect to angles of the marginal rays entering the probe, such that a substantially decreased cross-sectional size of the probe can be provided. In many embodiments, laterally outermost marginal rays of each of the outer beams on either side of the optical axis extend along an optical path substantially parallel to the optical axis and substantially parallel to the optical axis, or divergent from the optical axis. In many embodiments, lateral spread of the array of beams is inhibited as each individual beam converges toward the focal point, and this spread can be inhibited when the focal point is shifted.

In a first aspect, embodiments provide an apparatus for confocal imaging, comprising an illumination module for generating an array of light beams, an optics system for confocal focusing of the array of light beams and a probe head with a light-guiding part having an entrance face and an exit face. The illumination module, the optics system and the probe head are arranged such that the array of light beams from the illumination module passes through the optics system, enters the light-guiding part via the entrance face and exits the light-guiding part via the exit face. The optics system is configured such that, after having passed through the optics system, the outermost marginal rays of the outermost light beams with respect to the optical axis of the optics system are parallel or divergent to the optical axis.

In another aspect, embodiments provide an apparatus for confocal imaging comprising an illumination module for generating an array of light beams, an optics system for confocal focusing of the array of light beams and a probe head with a light-guiding part having an entrance face and an exit face. The illumination module, the optics system and the probe head are arranged such that chief rays of the array of light beams are divergent to each other.

In another aspect, embodiments provide a method for confocal imaging. An illumination module is provided for generating an array of light beams. An optics system is provided for confocal focusing of the array of light beams and a probe head with a light-guiding part having an optical axis and an entrance face and an exit face. The optics system is configured such that, after having passed through the optics system, outermost marginal rays of outermost light beams with respect to the optical axis are parallel or divergent with respect to the optical axis between the probe and focal points of the light beams.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 is a longitudinal cross-section through line A-A in FIG. 3; and

FIG. 5 is a longitudinal cross-section through a schematically illustrated probe head in accordance with embodiments.

DETAILED DESCRIPTION

Figure 1:
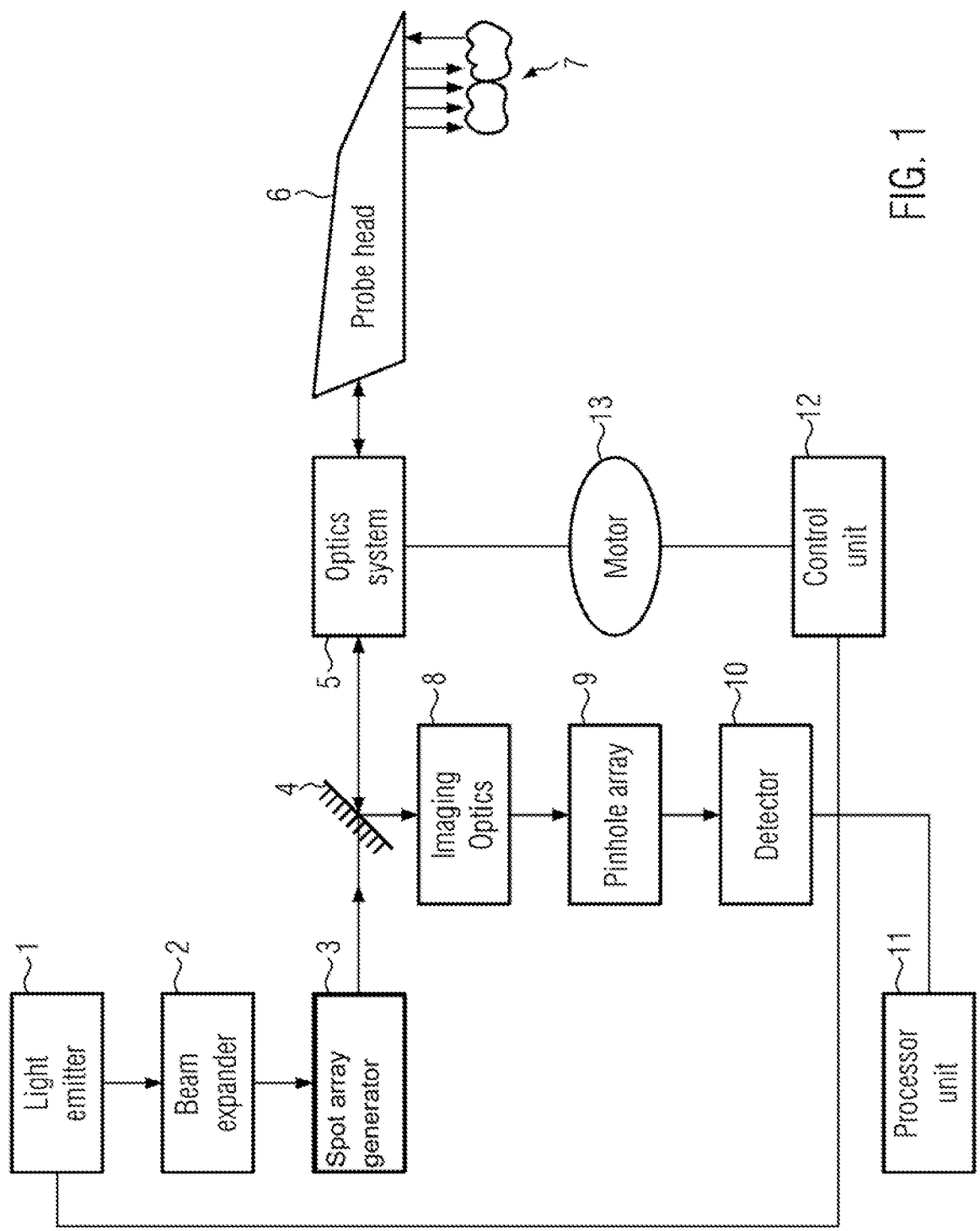
FIG. 1 is a schematic view of a confocal imaging apparatus, in accordance with embodiments.

The methods and apparatus disclosed herein can be combined in one or more of many ways and are well suited for combination with many devices related to surface topology such as the measurement of tissue surfaces such as surfaces of the oral cavity. The tissue surfaces may comprise one or more surfaces of teeth of the mouth, for example. The measured surfaces can be used by health care providers such as orthodontists and dentists.

In many embodiments, the optics system can be configured such that, after having passed through the optics system, the outermost marginal rays of the outermost light beams with respect to the optical axis of the optics system are parallel or divergent to the optical axis. In many embodiments, a plurality of light beams exits the probe head with divergent angles. Each of the plurality of light beams may comprise a chief ray divergent from an optical axis of the optics system.

In many embodiments, the outermost marginal rays of the outermost light beams, after exiting the optics system, do not converge towards the optical axis, in order to avoid a lateral spread of the array of beams even when shifting the focal plane of the focusing optics. In many embodiments, the term "outermost" refers to a distance transverse to the optical axis, such as a distance perpendicular to the optical axis. In many embodiments, an outermost light beam or most off-axis light beam comprises a beam having a largest distance to the optical axis in a direction perpendicular thereto.

The apparatus may be configured for intraoral confocal imaging, such as an apparatus for intraoral confocal imaging, which can be used for confocal imaging of positive and/or negative physical teeth models. The apparatus may comprise a scanning apparatus. The focusing optics of the apparatus may comprise non-telecentric optics, such that a reduced ray footprint at the probe head entrance face can be provided.

In many embodiments, the outermost marginal rays of the outermost light beams, after having passed through the optics system, are divergent with respect to the optical axis, and the divergence angle between the outermost marginal rays and the optical axis may be at most 10°, in some embodiments at most 8°, and in specific embodiments at most 5°.

In many embodiments, the light-guiding part comprises a transparent body. The transparent body may comprise one or more of glass or plastics, and may comprise a stiff, solid body, such as a rigid body.

The light-guiding part may be arranged such that the array of light beams enters the light-guiding part at an angle of approximately 90° with respect to the entrance face. In some embodiments, the light guiding part may be arranged such that the array of light beams enters via the entrance face at an angle of 90°±10°, such as 90°±8°, and more particularly of 90°±5°.

The light-guiding part may be bounded by sidewalls, and the sidewalls of the light-guiding part and entrance face may be arranged such that each light beam entering the light-guiding part via the entrance face is reflected at the sidewalls an odd number of times before exiting via the exit face. In many embodiments, each light beam may be reflected at the sidewalls three or five times before exiting via the exit face. Each of the sidewalls and/or the exit face and/or the entrance face may be planar.

The light-guiding part may be configured with an index of refraction and arrangement of the entrance face and sidewalls such that each light beam entering via the entrance face is reflected from at least one of the sidewalls of the light-guiding part by way of internal reflection. In many embodiments, at least some of the reflections at the sidewalls result from internal reflection such as one or more of total internal reflection, attenuated total internal reflection, or frustrated total internal reflection. Alternatively or additionally, at least some reflections may be provided with a mirror coating on a sidewall or part of a sidewall.

In many embodiments, the light-guiding part comprises a one-piece body.

In many embodiments, the light-guiding part comprises an upper sidewall being arranged at an acute angle with respect to the entrance face, a lower sidewall being arranged at an obtuse angle with respect to the entrance face, and an end sidewall being arranged at an acute angle with respect to the entrance face and/or the exit face. The upper sidewall may adjoin the entrance face; the lower sidewall may adjoin the entrance face and/or the end sidewall may adjoin the upper sidewall and/or the lower sidewall. The angle between the end sidewall and the upper sidewall may be an obtuse angle. The lower sidewall may comprise the exit face.

In many embodiments, the end sidewall may comprise a mirror. For example, the end sidewall may comprise a mirror coating. In such embodiments, the light-guiding part may be arranged and/or configured such that each light beam entering via the entrance face is reflected at all (remaining) sidewalls except for the end sidewall by way of internal reflection.

The angle between the entrance face and the lower sidewall may lie between 90° and 125°, in particular, between 90° and 115°. The angle between the exit face or the lower sidewall and the end sidewall may lie between 20° and 45°, in particular, between 25° and 35°. The angle between the entrance face and the upper sidewall may lie between 90° and 65°, in particular, between 90° and 80°.

The exit face may be covered by a transparent cover plate. The transparent cover plate may be a glass or plastics plate. The cover plate may be arranged at a distance from the exit face.

In many embodiments, the illumination module comprises a single light emitter or a plurality of light emitters. The one or more light emitters may emit coherent light. The light emitter may comprise one or a plurality of laser emitters. In embodiments comprising a single light emitter, the illumination module may further comprise a beam-expander element and/or a beam-splitter element for splitting a light beam from the light emitter into a plurality of light beams and/or an array of light beams. The beam-splitter element may comprise diffractive optics or a refractive optics, such as a grating or a microlens array.

Any of the above-described apparatuses may comprise a polarizer for linearly polarizing a light beam, wherein the polarizer is arranged along the optical path between the illumination module and the probe head, in particular, between the illumination module and the optics system.

Any of the above-described apparatuses may comprise a beam splitter being arranged along the optical path between the illumination module and the optics system such that the array of light beams from the illumination module passes through the beam splitter and an array of returning light beams from the optics module is reflected, in particular, towards a detector. The beam splitter may comprise a semi-transparent mirror. The light beams from the illumination module passing through the optics system may comprise incident light beams, and light beams following the optical path in an opposite direction through the optics system may comprise returning light beams. The array of returning light beams may comprise an array of light beams having been reflected by an object to be imaged, such as teeth portions, for example.

The described apparatuses may further comprise a detector for detecting an array of returning light beams. The detector may comprise an array of detector elements. The detector elements may comprise a CCD camera or a photodiode array. The detector may comprise a spectrophotometer.

The above-described apparatuses may comprise a focus-shifting mechanism for shifting the focal plane of the optics system. For example, the focus-shifting mechanism may be configured to shift one or more lenses of the optics system along the optical axis. In many embodiments, the focus-shifting mechanism may comprise a translation mechanism for translating the one or more lenses of the optics system.

In many embodiments, the probe heads comprise a housing, wherein the light guiding part and/or the optics system are provided within the housing. In embodiments where a focus-shifting mechanism is provided, the focus shifting mechanism may also be provided within the housing.

In many embodiments, the probe head comprises a part of a handheld device. The optics system and/or a focus-shifting mechanism may comprise part of the handheld device, for example. In particular, the handheld device may be defined by the housing described above.

Further features will be described with reference to the accompanying drawings, in accordance with embodiments.

As used herein, a chief ray encompasses a central ray of a beam of light. In many embodiments, a plurality of beams is directed onto the surface to be measured, in which each of the plurality of beams comprises a chief ray.

FIG. 1 schematically illustrates an example of an apparatus for dental confocal imagining of a teeth segment or teeth portion, in accordance with many embodiments. The teeth segment may comprise one tooth, a plurality of teeth, a tooth stump and/or a portion where one or more teeth are missing. The apparatus may be used, for example, for intraoral imaging of teeth. Alternatively, imaging of a positive or negative teeth model may be performed as well.

The illustrated apparatus comprises a light emitter 1 as a source of coherent light. As an example, the light emitter may be a laser source such as a semiconductor laser.

As indicated by the arrow shown, emitted light passes through a beam expander 2, which may comprise a collimating lens so as to obtain a collimated light beam having a desired width or numerical aperture.

Along the optical path between the light emitter 1 and the beam expander 2, optionally, a polarizer such as a polarization filter may be provided.

The beam expander 2 is followed by a spot array generator element 3 for splitting the beam into an array of light beams. The spot array generator element 3 in the form of diffraction or refraction optics may comprise a grating or a microlens array, for example.

In the illustrated example, the light emitter comprises a single light source from which the array of light beams is generated via the beam expander and the beam splitter element. As an alternative, the light emitter 1 may already comprise a plurality of light sources being arranged in form of an array. In this case, the array of light beams is generated directly at the light emitter 1 so that a beam expander and/or beam splitter may be avoided. As an example, the array of light sources may be provided in the form of an array of laser sources such as semiconductor lasers.

In this example, the light emitter 1, the beam expander 2 and the spot array generator element 3 define an illumination module generating an array of light beams.

The array of light beams, represented here, for ease of illustration, by a single line, passes through a beam splitter 4 in form of a semi-transparent mirror and enters optics system 5. The optics system 5 comprises a non-telecentric, confocal lens arrangement which will be described in more detail below.

The light beams coming from the light emitter 1 and propagating towards the sample to be imaged (e.g. a teeth segment) are called incident light beams, whereas light beams being reflected at the sample and propagating along the optical path of the incident light beams but in opposite direction are called returning light beams.

After the optics system 5, the incident array of light beams enters a probe head 6. In particular, the array of light beams is coupled into a light guiding part of the probe head via the light guiding part's entrance face. Within the light guiding part, each beam is reflected several times before it is coupled out via an exit face onto an object to be imaged, such as a teeth segment 7. In this way, an incident array of light beams is emitted towards the teeth segment 7, thus, resulting in an array of light spots on the teeth surface.

As also illustrated by one of the arrows between a tooth and the probe head, reflected light re-enters the probe head 6, particularly its light guiding part via the exit face. In this way, each reflected or returning light beam travels along the optical path in opposite direction as travelled by the incident light beams. Therefore, the returning light beams are also reflected several times within the light guiding part of probe head 6 and pass through optics system 5 in an inverse direction. At the semi-transparent mirror 4, the returned light beams are reflected towards imaging optics 8 comprising one or more lenses, followed by a pinhole array 9.

Then, the array of returning light beams impinges onto a detector 10, comprising an array of detector elements. For example, the detector 10 may be a CCD camera or a photodiode array. Each detector element or sensing element corresponds to a pinhole in the array 9.

The detector 10 is connected to a processing unit 11 where each light intensity measured in each of the detector elements is grabbed and analyzed.

The apparatus further comprises a control unit 12 being connected to the light emitter 1 as well as to a motor 13. Motor 13 is an example of a focus-shifting mechanism for shifting the focal plane of the optics system 5. In particular, motor 13 is coupled to the optics system 5 so as to shift or translate one or more lenses of the optics system along the optical axis. In this way, the focal plane location may be changed or shifted.

After receipt of a feedback signal that the location of the focal plane has changed (or that the one or more lenses have been shifted), control unit 12 triggers light emitter 1 to generate a light pulse. Processing unit 11 will grab data representative of the light intensity as detected by detector 10 corresponding to the light pulse which was reflected at the teeth portion 7. This procedure will be repeated for a plurality of locations for the focal plane.

As outlined in detail in WO 00/08415, the entire disclosure of which is incorporated herein by reference, for example, the surface topology of the image object (e.g. a teeth segment) is determined by determining the focal plane location for which, for a particular pixel, the light intensity is maximal. In this way, a three-dimensional representation of the object, e.g., the teeth segment, may be obtained. It may be displayed and/or further processed.

The array of light beams may comprise light beams having different wavelengths. For this purpose, the light emitter 1 may comprise different light sources emitting light of different wavelengths. In case of an array with beams of different wavelengths, the detector may be a spectrophotometer with color resolution. Examples for spectrophotometers are a three-chip CCD camera or the use of a Bayer mask over a monochrome CCD or other light sensor.

By using light components or light beams with different wavelengths, each being focused simultaneously on a different focal plane, the time for imaging may be reduced as different focal plane ranges can be simultaneously measured.

The probe head 6 may comprise a housing. For example, both the optics system 5 and the light guiding part may be provided within such a housing. The housing may be configured as a handheld device so that the light guiding part and/or optics system 5 and/or motor 13 are included in the handheld device.

Figure 2A:
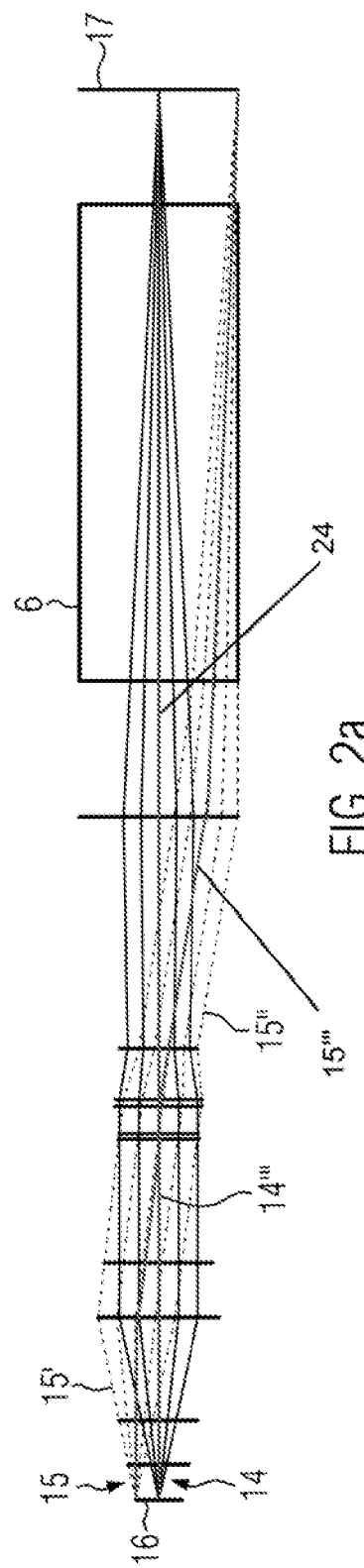
FIG. 2A is a schematic view of the optical path in an optics system of a confocal imaging apparatus in a paraxial design, in accordance with embodiments.

FIG. 2A schematically illustrates a paraxial design example of the optics system, showing the first order imaging configuration, in accordance with many embodiments. In this schematic view, probe 6 is illustrated as a single block. In this example, a central beam 14 and an outermost beam 15 (in a direction perpendicular to the optical axis) are emitted from a source plane 16. By way of example, reference numerals 15' and 15" denote marginal rays of the outermost beam 15, whereas reference numeral 14''' denotes the chief ray of central beam 14. Thus, the term "marginal rays" is used in the conventional sense denoting the rays (of a specific light beam) defining the beam's circumference or envelope; the "chief ray" corresponds to the central ray of a beam.

As can be seen in this example, the outermost marginal ray 15" of outermost light beam 15, after having passed through the optics system 5 and before entering the probe head 6, is parallel to the optical axis 24, and the marginal ray 15" is parallel to chief ray 14''' of the central beam that is on the optical axis 24.

In case of the complete array of light beams, the outermost marginal rays of the outer beams of the array (on either side of the optical axis) after having passed through the optics system and before entering probe head, are all parallel to the optical axis. As a consequence of this configuration, there is little or no lateral spread of the array of beams even when shifting the focal plane 17 of the array.

Each of the plurality of light beams may comprise a chief ray. For example, the outer beam 15 may comprise a chief ray 15''' extending from an outer aperture at source plane 16 to the focus at focal plane 17.

As an alternative to or in combination with the above-described parallelism of the outermost marginal rays of the outermost beams and the chief ray of the central beam, the optics system may be configured such that the outermost marginal rays of the outermost light beams with respect to the optical axis of the optics system are divergent relative to the optical axis. In many embodiments, after having passed through the optics system, the outermost marginal ray of the outermost beams may show an opening angle with respect to the optical axis. This divergence angle or opening angle with respect to the optical axis may be at most 10°, preferably at most 8°.

In many embodiments, the confocal focusing system of the optics system comprises a non-telecentric optical system. The optics system can be configured such that the angle defined by the marginal rays of an outermost beam is complementary to the angle defined by the extreme off-axis chief rays with respect to the optical axis. In such embodiments, a decreased ray footprint at object to be imaged, e.g. the teeth segment, is provided.

Figure 2B:
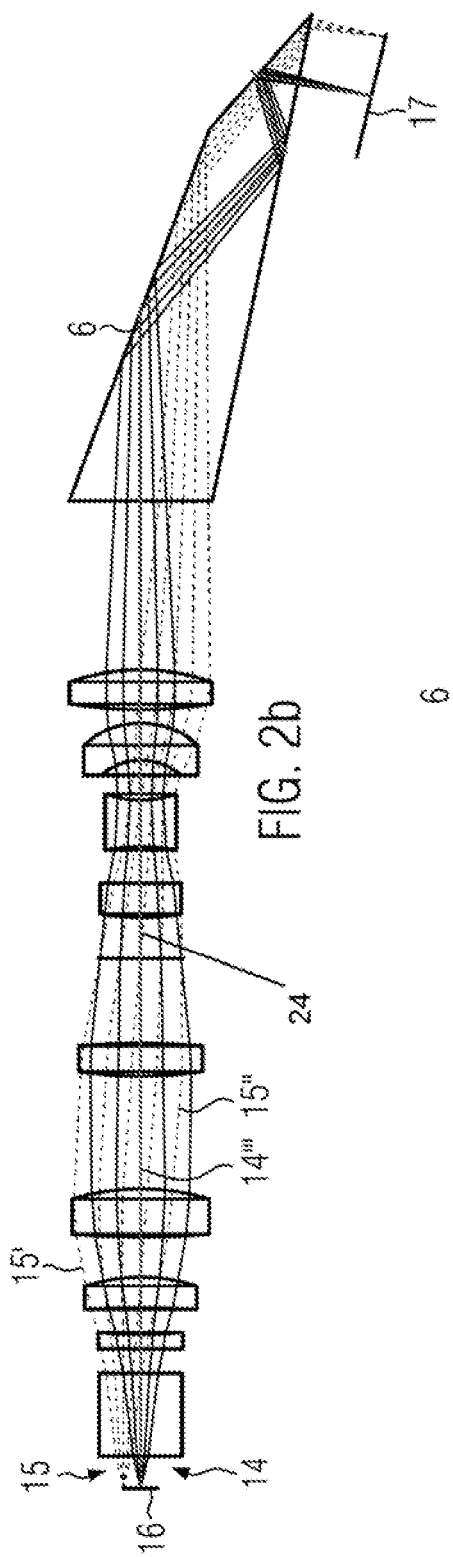
FIG. 2B is a schematic view of the optical path in an optics system of a confocal imaging apparatus in a thick lens design, in accordance with embodiments.

FIG. 2B schematically illustrates a thick lens design example corresponding to the embodiments of FIG. 2A. Also in FIG. 2B, from the array of beams generated by the illumination module, only one central beam 14 and one outermost beam 15 are shown with dashed lines for the sake of simplicity, in accordance with embodiments.

Figure 3:
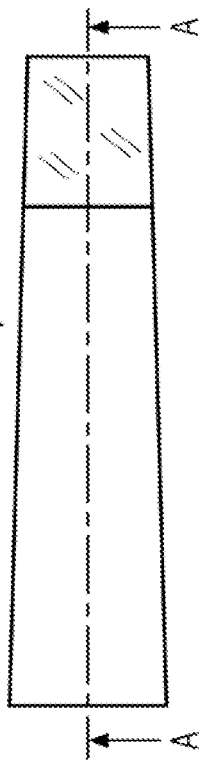
FIG. 3 is a top view of a schematically illustrated probe head, in accordance with embodiments.

FIGS. 3 and 4 schematically illustrate a top view and a cross-sectional view (through line A-A) of a probe head, respectively, in accordance with many embodiments. The probe head 6 has a light-guiding part with an entrance face 18 and an exit face 19. Light coming from the light emitter and the optics system enters the light-guiding part via the entrance face 18 at an angle of about 90°, i.e., substantially normal to the entrance face. The entrance angle may be 90°±10°, preferably 90°±8°, for example. This particularly applies to the embodiments in which the outermost marginal rays of the outermost light beams are divergent with respect to the optical axis after having passed through the optics system.

As schematically illustrated in FIG. 4, the light-guiding part is arranged and light is coupled into the light guiding part in such a way that each light beam entering the light-guiding part via the entrance face 18 is reflected at the sidewalls. In embodiments according to FIG. 4, three reflections occur before a light beam exits the light-guiding part via the exit face 19. A first reflection takes place at an upper sidewall 20, adjoining the entrance face 18 and being arranged at an acute angle with respect to entrance face 18. The second reflection occurs at lower sidewall 21, also adjoining the entrance face 18 and being arranged at an obtuse angle with respect thereto. The last reflection occurs at end sidewall 22, adjoining both the upper and the lower sidewalls. The exit face 19 is part of the lower sidewall 21.

End sidewall 22 comprises a mirror, which may be obtained by a suitable coating of the corresponding surface of the light-guiding part. The light-guiding part as a whole, in these embodiments, may comprise a one-piece body, for example, comprising a glass body or a body composed of a transparent resin. The first and second reflections at upper sidewall 20 and lower sidewall 21 may result from internal reflection.

In view of these embodiments, the light-guiding part of the probe head, in accordance with its one-piece form, may be manufactured in a simple and economical way.

The specific configuration of the optics system as described above allows for a long light-guiding part and probe head while maintaining a small thickness resulting in an improved intraoral use.

In many embodiments, and as illustrated in FIG. 5, the exit face 19 may be covered by a transparent cover plate 23 which is arranged at some distance from the exit face 19. This cover plate 23 may be exchangeable for hygienic reasons, and may comprise a single use component.

The embodiments illustrated in FIG. 5 provides for an even longer light-guiding part along which the light beams are reflected five times before exiting via the exit face 19. In principle, any odd number of reflections is possible.

In many embodiments, the chief rays of each of a plurality of light beams exits the exit face 19 with a divergent angle with respect to the optical axis, for example. This divergence of each of the chief rays of the light beams provides improved measurements and can decrease the overlap of spots imaged onto the oral cavity, for example. The decrease of spread of the marginal rays the light beams as described herein can be combined with the divergence of the chief rays of each of the light beams in order to provide improved the accuracy of measurements as described herein, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for intraoral imaging, the apparatus comprising:
   a light source for generating light;
   an optics system for focusing the light, the optics system having an optical axis and comprising one or more movable lenses and one or more additional lenses, wherein the one or more moveable lenses are moveable along the optical axis;
   a probe head, wherein the light source, the optics system and the probe head are arranged such that the light passes through the optics system, passes through the probe head, and exits the probe head, and wherein the optics system is configured such that, upon entering the probe head, an outermost chief ray of the light with respect to the optical axis of the optics system is divergent to the optical axis and an outermost marginal ray of the light with respect to the optical axis is parallel or divergent to the optical axis;
   a detector for detecting returning light reflected off of an intraoral object, wherein the detector comprises an array of detector elements;
   a beam splitter disposed along an optical path between the light source and the optics system such that the light from the light source passes through the beam splitter and such that the returning light is reflected by the beam splitter toward the detector; and
   a focus shifting mechanism configured to shift a focal plane of the optics system, wherein the focus shifting mechanism comprises a motor configured to shift the one or more moveable lenses of the optics system along the optical axis to shift the focal plane of the optics system.

2. The apparatus according to claim 1, wherein the beam splitter comprises a semi-transparent mirror.

3. The apparatus according to claim 1, further comprising:
   a polarizer disposed along the optical path between the light source and the beam splitter, wherein the polarizer is a linear polarizer configured to linearly polarize the light.

4. The apparatus according to claim 1, wherein the probe head comprises a light-guiding part comprising a mirror, wherein the mirror is configured to direct the light through an exit face of the probe head.

5. The apparatus according to claim 1, wherein the probe head comprises a longitudinal axis, the apparatus further comprising:
   a mirror, wherein the mirror is to reflect the light at an angle to the longitudinal axis.

6. The apparatus according to claim 5, wherein the angle is approximately perpendicular to the longitudinal axis.

7. The apparatus according to claim 1, wherein the light source comprises an illumination module for generating an array of light beams, and wherein the optics system is a confocal optics system for confocal focusing of the array of light beams.

8. The apparatus according to claim 1, wherein the light source comprises one or more light emitters that emit coherent light.

9. The apparatus according to claim 8, wherein the one or more light emitters comprise one or more laser emitters.

10. The apparatus according to claim 1, wherein the probe head comprises an exit face, an upper sidewall, a lower sidewall, and an end sidewall arranged at an acute angle with respect to the exit face.

11. The apparatus according to claim 10, wherein the end sidewall comprises a mirror.

12. The apparatus according to claim 10, wherein the exit face is covered by a removable transparent cover plate.

13. The apparatus according to claim 1, wherein the outermost marginal ray of the light with respect to the optical axis of the optics system is at a first angle with the outermost chief ray that is complementary to a second angle defined by the outermost chief ray with respect to the optical axis, wherein the outermost chief ray is an outermost off-axis chief ray.

14. The apparatus according to claim 1, wherein a divergence angle between the outermost marginal ray and the optical axis is at most 10 degrees.

15. The apparatus of claim 1, further comprising:
a processing unit connected to the detector, the processing unit to analyze readings from the array of detector elements.

16. The apparatus of claim 1, wherein light comprises an array of light beams, and wherein the optics system is configured such that, upon entering the probe head, the outermost chief ray of an outermost light beam of the array of light beams with respect to the optical axis of the optics system is divergent to the optical axis and the outermost marginal ray of the outermost light beam with respect to the optical axis is parallel or divergent to the optical axis.

17. The apparatus of claim 1, wherein the outermost marginal ray of the light with respect to the optical axis is parallel to the optical axis.

18. The apparatus of claim 1, wherein the outermost marginal ray of the light with respect to the optical axis is divergent to the optical axis.

19. A method of intraoral imaging, comprising:
generating light by a light source of an apparatus for intraoral imaging;
passing the light though a beam splitter of the apparatus;
focusing the light by an optics system of the apparatus, the optics system having an optical axis and comprising one or more movable lenses that are moveable along the optical axis;
passing the light into a probe head of the apparatus, wherein upon the light entering the probe head, an outermost chief ray of the light with respect to the optical axis of the optics system is divergent to the optical axis and an outermost marginal ray of the light with respect to the optical axis is parallel or divergent to the optical axis;
reflecting the light off of a mirror and onto an intraoral object external to the apparatus;
receiving, at the probe head, returning light reflected off of the intraoral object;
reflecting the returning light off of the beam splitter toward a detector of the apparatus, wherein the detector comprises an array of detector elements; and
shifting a focal plane of the optics system using a focus shifting mechanism of the apparatus by causing a motor of the apparatus to shift the one or more moveable lenses of the optics system along the optical axis.

20. The method according to claim 19, further comprising:
linearly polarizing the light using a polarizer before passing the light through the beam splitter.

21. The method according to claim 19, wherein the probe head comprises a light-guiding part, and wherein passing the light into the probe head comprises passing the light into the light-guiding part.

22. The method according to claim 19, wherein the light source comprises an illumination module, and wherein generating the light comprises generating an array of light beams using the illumination module.

23. The method according to claim 19, wherein focusing the light comprises performing confocal focusing of the light.

24. The method according to claim 19, further comprising:
directing the light through a removable transparent cover plate attached to the probe head.

25. The method according to claim 19, wherein the outermost marginal ray of the light with respect to the optical axis of the optics system is at a first angle with the outermost chief ray that is complementary to a second angle defined by the outermost chief ray with respect to the optical axis, wherein the outermost chief ray is an outermost off-axis chief ray.

26. The method of claim 19, further comprising:
analyzing readings from the array of detector elements by a processing unit connected to the detector.

27. The method of claim 19, wherein the light comprises an array of light beams, and wherein the optics system is configured such that, upon entering the probe head, the outermost chief ray of an outermost light beam of the array of light beams with respect to the optical axis of the optics system is divergent to the optical axis and the outermost marginal ray of the outermost light beam with respect to the optical axis is parallel or divergent to the optical axis.

* * * * *